United States Patent [19]

Sideris

[11] Patent Number: 5,284,488
[45] Date of Patent: Feb. 8, 1994

[54] ADJUSTABLE DEVICES FOR THE OCCLUSION OF CARDIAC DEFECTS

[76] Inventor: Eleftherios B. Sideris, 1600 Coulter, Ste. 200 B, Amarillo, Tex. 79106

[21] Appl. No.: 995,817
[22] Filed: Dec. 23, 1992
[51] Int. Cl.⁵ ............................................. A61B 17/00
[52] U.S. Cl. ........................... 606/213; 606/215; 606/216; 606/157; 623/11; 128/887; 128/899
[58] Field of Search ............. 606/213, 215, 216, 200, 606/232, 151, 157, 1; 128/887, 899; 623/1, 11

[56] References Cited

U.S. PATENT DOCUMENTS

| | | | |
|---|---|---|---|
| 3,874,388 | 4/1975 | King et al. | 606/213 |
| 4,519,392 | 5/1985 | Lingua | 606/151 |
| 4,621,638 | 11/1986 | Silvestrini | 606/230 |
| 4,669,473 | 6/1987 | Richards et al. | 606/215 |
| 4,901,721 | 2/1990 | Hakki | 606/232 |
| 4,917,089 | 4/1990 | Sideris | 606/215 |
| 5,021,059 | 6/1991 | Kensey et al. | 606/213 |
| 5,053,046 | 10/1991 | Janese | 606/215 |
| 5,108,420 | 4/1992 | Marks | 606/213 |
| 5,171,259 | 12/1992 | Inoue | 606/213 |
| 5,192,301 | 3/1993 | Kamiya et al. | 606/213 |

Primary Examiner—Stephen C. Pellegrino
Assistant Examiner—Jeffrey A. Schmidt
Attorney, Agent, or Firm—Wendell Coffee

[57] ABSTRACT

An intravascular prostheses is delivered transarterially or transvenously to occlude cardiac defects. The defects, which may include the patent ductus arteriosus, the ventricular septal defect and the atrial septal defect. The prostheses is a device having a distal occluder attached to a string and a proximal occluder connected to the string. The occluders are delivered to the heart by known methods. With the distal occluder on the distal side of the defect and the proximal occluder on the proximal side of the defect the occluders are adjusted according to the thickness of the heart structure at the defect. In one embodiment the adjustment is by moving the distal occluder over a series of knots or buttons in the string. In another embodiment the proximal occluder is connected to the distal occluder by an elastic string so that the elastic tension of the strings bring the occluders into position. A radiopaque button is placed upon the string to aid positioning the occluders.

4 Claims, 2 Drawing Sheets

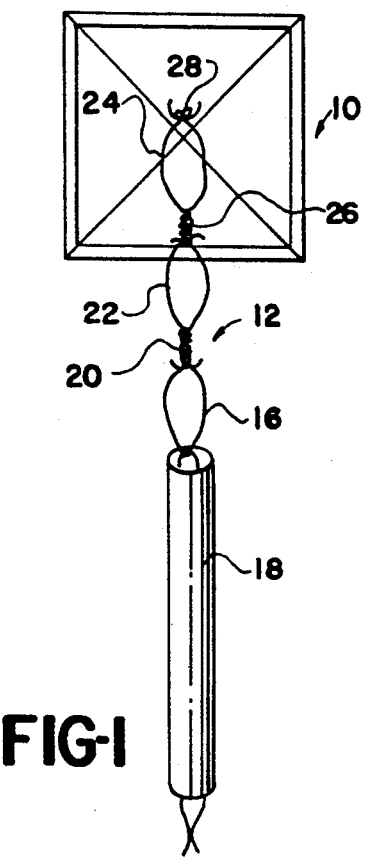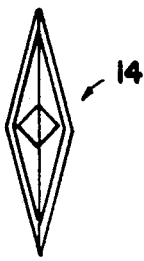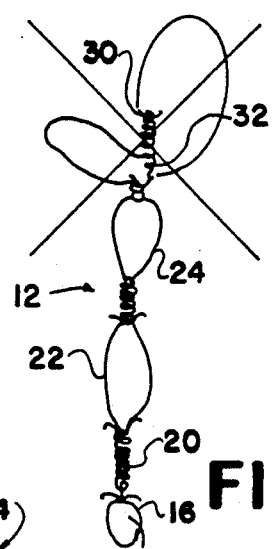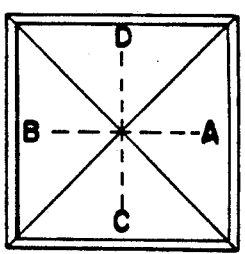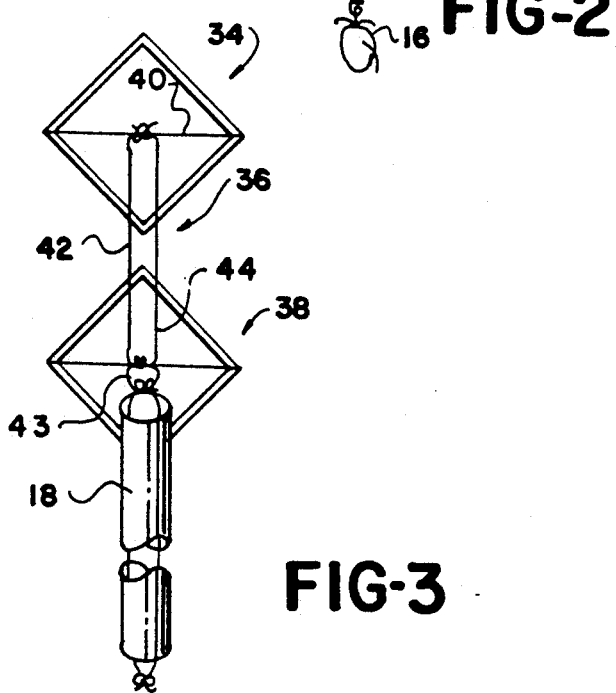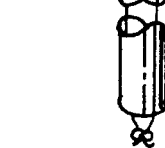

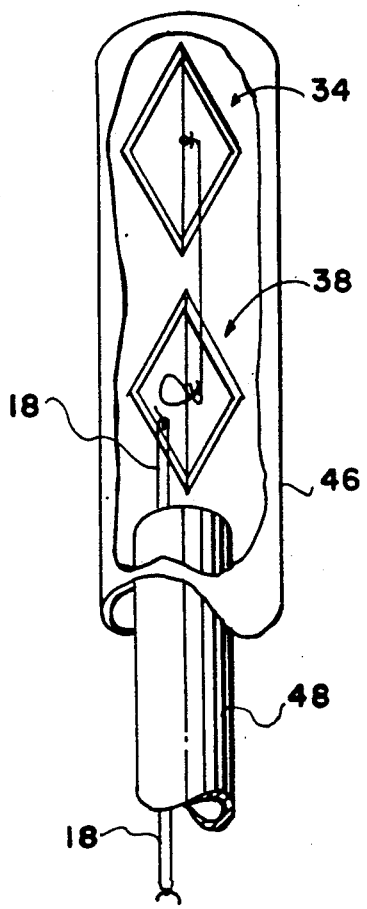
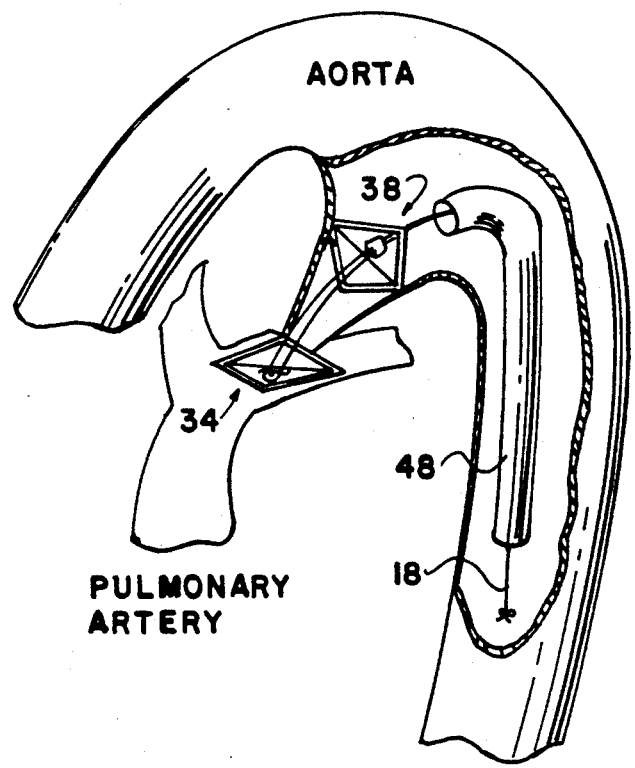
FIG-4  FIG-5

ADJUSTABLE DEVICES FOR THE OCCLUSION OF CARDIAC DEFECTS

BACKGROUND OF THE INVENTION (1) Field of the Invention

The present invention relates to intravascular prostheses, delivered transarterially or transvenously, for the occlusion of cardiac defects. Such defects include the patent ductus arteriosus, the ventricular septal defect and the atrial septal defect.

(2) Description of the Related Art

U.S. Patents: KING et al, U.S. Pat. No. 3,874,388, SIDERIS, U.S. Pat. No. 4,917,089.

Publications: Rashkind—Circulation—vol 67, No. 4, April 1983.

Patent ductus arteriosus is an important vessel for the fetus, because a large percentage of the cardiac output is bypassing the lungs through the ductus. However, the ductus after birth is constricted after exposure to oxygen in the majority of children. Patency of ductus arteriosus after birth is common in premature babies (30%), and uncommon in term babies (<1%). Persistence of the ductus arteriosus is associated with left to right shunt with increased volume of blood crossing from the aorta to the pulmonary artery and the lungs. Left to right shunt can cause deterioration of the lung disease in premature infants, congestive heart failure in infancy and pulmonary vascular obstructive disease in older children. Patency of ductus arteriosus carries the risk of infection (endarteritis or endocarditis), in all ages. For this reason occlusion or surgical ligation of the ductus arteriosus is recommended in all cases.

Surgical ligation or division carries low risk especially in older children. However, it is always associated with significant morbidity because of the need of thoracotomy, general anesthesia, placement of chest tubes, intensive care. The discomfort and the expense are significant. For these reasons attempts have been made for the transcatheter occlusion of patent ductus arteriosus.

Ventricular septal defect is the commonest heart defect. It causes congestive heart failure to a number of children and it often requires surgery in early life. Unfortunately most of the defects do not have adequate rim and therefore are not amenable to umbrella occlusion. However, some of them (muscular VSDs) could be closed provided that a device existed to be applicable in small children and adjustable for the ventricular septal thickness.

Historically, the first transcatheter occlusion of PDA was performed by Posner in Germany transarterially, utilizing an Ivalon foam plug. The method has been used primarily by German and Japanese investigators in adults and older children. It requires a large femoral artery for the entry and it is associated with significant arterial complications.

Sporadic reports about detachable balloons, special bags, or metals have followed.

KING and MILLS invented a Double Disk device, (U.S. Pat. No. 3,874,388) for the occlusion of intracardiac defects and primarily ASDs. The device was bulky, requiring a 23 F introduction. Modifications on the same principle were made by others. The most successful one was the one by RASHKIND, commercialized by BARD. The device employs two discs on the same catheter. The discs are made by polyurethane foam and a metal skeleton. They are connected through a complex release mechanism to the main catheter. The distal disk is released in the arterial side of the ductus and the proximal disk in the pulmonary artery side, in case of transvenous PDA occlusion. The RASHKIND device requires a large introduction (11 F) for PDAs larger than 4 mm and an 8 F introducing sheath, for small PDAs. Therefore, the method has not found application in small children with large communications. Indeed this is the group where occlusion is most urgent. Furthermore, it is not applicable to long and tubular PDAs or even very short ones. Because of the large introducing sheath, there is often the need of dilation of the small ductus by angioplasty balloons prior to the occlusion. The incidence of residual shunts is significant, especially in large PDAs. A common objection to the method is the persistence of the ductal channel despite its occlusion, since the device is only obstructing the narrow part of the ductus.

Another recent modification of the KINGS and MILLS device was the "Clumshell" device. It was applied successfully for ASD, PDA and VSD occlusion. However, it was withdrawn because of wire fracture. It was quite bulky, requiring an 11 F introduction and therefore was not applicable in small children.

In 1990 a patent was issued for the "Buttoned Device For The Occlusion Of The Intracardiac Defects" (U.S. Pat. No. 4,917,089). This device is made by two independently introduced disks that are eventually buttoned across a defect. It requires a small sheath (7-8 F) for introduction and it can be used in small children. However, the distance between the two disks is predetermined since the button loop has a length of 2-4 mm for the ASD application. Therefore, what it can be applicable for an ASD occlusion cannot be used for a long "tubular" PDA occlusion. Ventricular septum has a different thickness than the atrial septum and therefore an ASD occluding buttoned device cannot be used for a ventricular septal defect occlusion.

SUMMARY OF THE INVENTION (1) Progressive Contribution to the Art

The intracardiac devices of the current invention provide the means of transarterial or transvenous without surgery occlusion of heart defects. Two such adjustable devices will be described; an adjustable buttoned device and a self-adjustable two disk device.

The buttoned device: The occlusion can be transvenous or transarterial and can be achieved by the independent introduction of the two buttoned components, the occluder and the counter-occluder. All components have been described in inventor's U.S. Pat. No. 4,917,089.

Several difference exist though, to the loop connected to the center of the occluder. In a preferred embodiment of the loop aspect of the occluder, the 3.0 nylon loop is 8 mm long. It comprises a terminal 1 mm loop, a radiopaque button, a middle 2 mm loop and a proximal 2 mm loop. The individual loops and the radiopaque button are separated by triple knots. Because of the length of the loop and the several knots (buttons) the device can be adjusted during buttoning to PDAs of variable length and septal defects with variable thickness.

Since the introduction for 15 and 20 mm occluders can be achieved through small (7 F or 2.3 mm) sheaths the device can be even used in small children.

The double disk device: It consists of the following components; the proximal disk, the distal disk, the connecting suture between them (elastic suture and safety nylon thread) and the release wire. In a preferred embodiment of the distal disk of the device, it is made by a single skeleton wire sutured on polyurethane or woven material disk.

The wire is 0.018" and comprises a fluorocarbon resin (TEFLON) coated hollow outer part with a 0.009" central stainless steel part. It is rounded in the middle with a diameter equal to the skeleton wire length and it is narrowly angled at the wire ends for easier introduction.

Another aspect of the present invention is the proximal disk. It is made exactly like the distal disk. An important aspect of this device is the connecting suture between the two disks. The connecting suture has two components; the elastic suture and the safety nylon thread. They are connected at the center of the bottom surface of the distal disk and the center of the top surface of the proximal disk. The elastic suture is a Latex suture, and has a 2 mm length when relaxed and a 10 mm length when stretched. The other suture is a 3.0 nylon one and has a length of 10 mm.

On the bottom surface of the proximal disk, a 1 mm nylon loop, made by 3.0 nylon is sutured.

Another aspect of the device is the release wire. It is a 0.035" fluorocarbon resin (TEFLON) coated hollow wire with a double 0.008" nylon thread connected to the nylon loop of the proximal disk.

The device is introduced into a 5-6 F long sheath. The sheath is positioned across the defect; the distal disk is released and it is pulled against the tip of the long sheath to become perpendicular to it; subsequently both sheath and distal disk are pulled, until the disk is occluding the defect. The sheath is carefully pulled back with the device stretched until the proximal disk is totally released in the proximal to the defect chamber. The stretching is then relaxed and the proximal disk is automatically occluding the defect. Manipulations are possible under fluoroscopy and echocardiography. The release of the device is achieved through the same mechanism as the buttoned device.

In accordance with the principles of the present invention, the adjustable devices have significant advantages over known devices and specifically the RASHKIND device, the KING and MILLS device and the classical buttoned device. They are miniaturized in size and can be adjusted for the variable length of the ductus or the thickness of the ventricular septum.

(2) Objects of this Invention

An object of this invention is to provide adjustable occluding devices small enough to be introduced in any size child.

Another object of this invention is to be able to adjust the length between the two disks according to the length of the ductus or the thickness of the septum.

Another is to obtain universal application in defects of various size and shape.

Further objects are to achieve the above with devices that are sturdy, compact, durable, lightweight, simple, safe, efficient, versatile, ecologically compatible, energy conserving, and reliable, yet inexpensive and easy to manufacture, install, and maintain.

Other objects are to achieve the above with a method that is rapid, versatile, ecologically compatible, energy conserving, efficient, and inexpensive, and does not require highly skilled people to install, and maintain.

The specific nature of the invention, as well as other objects, uses, and advantages thereof, will clearly appear from the following description and from the accompanying drawings, the different views of which are not necessarily scale drawings.

BRIEF DESCRIPTION OF THE DRAWINGS

FIG. 1 is a perspective view of the preferred embodiment of the intracardiac buttoned device prosthesis with the occluder connected through the button loop with the loading wire.

FIG. 1a is a perspective view of a counter occluder.

FIG. 2 is a perspective view of the button loop connection with the occluder wire skeleton.

FIG. 2a is a perspective view of the occluder, the wire frame of which was shown in FIG. 2.

FIG. 3 is a perspective view of the self-adjustable double disk device in the unfolding condition.

FIG. 4 is a perspective view of the self-adjustable double disk device, folded and introduced in the sheath.

FIG. 5 is a cross-sectional view of double disk self adjustable device, occluding a patent ductus arteriosus.

As an aid to correlating the terms of the claims to the exemplary drawing(s), the following catalog of elements and steps is provided:

10 occluder (or distal occluder)
12 button loop (or string)
14 counter-occluder (or proximal occluder)
16 terminal small loop
18 loading or release wire
20 radiopaque button
22 middle loop
24 first loop
26 middle button
28 terminal three knots
30 two knots on top of the occluder
32 three knots on the bottom of the occluder
34 distal disk (or distal occluder)
36 connecting threads (or string)
38 proximal disk (or proximal occluder)
40 skeleton wire
42 nylon safety thread 43 Nylon Loop
44 elastic thread
46 long sheath
48 pusher catheter

DESCRIPTION OF THE PREFERRED EMBODIMENTS(S)

Referring to the drawings, and FIG. 1 in particular, there is illustrated occluder 10 (or distal occluder) of the buttoned device connected to button loop 12 (or string) and counter-occluder 14 (or proximal occluder). Occluder and counter-occluder have been described in detail in U.S. Pat. No. 4,917,089. The button loop 12 is made by 3.0 nylon thread and it consists of:

a) terminal small loop 16 with a diameter of 102 mm; the terminal small loop accommodates the nylon thread of loading wire 18.

b) radiopaque "button" 20 with a length of 1 mm; this is made by 0.035" hollow fluorocarbon resin (TEFLON) coated wire and it is separated by three knots from the terminal loop 16 and middle loop 22.

c) the middle loop 22 has a diameter of 2-3 mm and it is separated from the radiopaque button 20 and separated from the first loop 24 by three knots.

d) the three knots between the middle loop 22 and first loop 24 form middle button 26.

e) the first loop 24 has a diameter of 3 mm and its limits are the middle button 26 and terminal three knots 28.

FIG. 2, shows the connection of the button loop 12 to the occluder 10, the two ends of the nylon thread are introduced upwards through the foam in corners (A,B). They are tightened with two knots 30 on top of occluder 10. Subsequently the ends of the nylon thread are turned down through the foam at the corners (C,D). They are tightened at the bottom of occluder 10 by three knots 32. The method of adjustable buttoning, involves entry of one of the buttons of the button loop 12 through the rubber center of the counter-occluder 14 and the attachment by the valve-like action. If the length of the ductus or the thickness of the septum are more than 5-6 mm the counter-occluder stops right after the radiopaque button 20. If the ductus or the septal thickness are less than 3 mm, the counter-occluder crosses the middle button 26. Intermediate situations can be also accommodated in a similar manner.

FIG. 3 shows the two disk self-adjustable device. From the top to the bottom, there is distal disk 34, distal occluder 34; the connecting suture 36 (or string) between two disks; proximal disk 38 (or distal occluder); and release wire 18. The distal disk 34 is made by poly-urethane foam or woven material and has rounded shape. Single or double coated skeleton wire 40 has floppy ends.

At the center of skeleton wire of the lower surface of the distal disk 34, the connecting sutures are inserted. There are two connecting sutures, one elastic 42 with a relaxed length of 1-2 mm and a stretched length of 10 mm and nylon safety thread 44. The safety thread 44 has a length of 10 mm. The connecting sutures connect the lower surface of the distal disk 34 and the upper surface of the proximal disk 38 in the middle of their respective skeleton wires.

The proximal disk 38 is made by poly-urethane foam or woven material and has the same size and shape as the distal disk 34. A 1 mm diameter nylon loop 43 is sutured at the bottom of the proximal disk 38.

FIG. 4 shows the introduction of the device into long sheath 46. The distal disk 34 is first introduced, followed by the proximal disk 38. Pusher catheter 48 is introduced over the loading wire into the long sheath 46.

FIG. 5 shows a patent ductus arteriosus occluded with the self-adjustable double disk device transarterially. The distal disk 34 has been released in the pulmonary artery and pulled against the pulmonary end of the ductus. The long sheath 46 is then pulled in the aorta where the proximal disk 38 is released and it is automatically pulled by the elastic thread on the arterial end of the ductus. Because of the elastic connecting thread 44 the device can be self adjusted for the length of the ductus. The release is achieved the same way as in buttoned device.

The embodiment shown and described above is only exemplary. I do not claim to have invented all the parts, elements or steps described. Various modifications can be made in the construction, material, arrangement, and operation, and still be within the scope of my invention.

The restrictive description and drawings of the specific examples above do not point out what an infringement of this patent would be, but are to enable one skilled in the art to make and use the invention. The limits of the invention and the bounds of the patent protection are measured by and defined in the following claims.

I claim as my invention:

1. An intracardiac percutaneously deliverable device for the repair of heart defects comprising:
   a) an occluder, said occluder including:
      i) a foldable foam resin disk,
      ii) a coated wire skeleton in the form of an X sutured to the foam disk,
      iii) an adjustable loop sutured to the center of the wire skeleton,
   b) said adjustable loop is formed by
      i) a first loop, connected to said wire skeleton
      ii) a middle loop, connected to said first loop
      iii) a terminal small loop, connected to said middle loop, and
      iv) a radiopaque button attached between two of the loops of said adjustable loop
   c) a counter-occluder
   d) a loading wire, wherein said loading wire is a fluorocarbon resin coated hollow wire,
   e) a long double thread going through the terminal small loop, into one end and through the hollow wire, and tied at the other end of the hollow wire; wherein the counter-occluder may be pushed along the loading wire toward the occluder and stop at a distance adjusted according the length or thickness of the occluded structure.

2. An intracardiac percutaneously deliverable device for the repair of heart defects comprising:
   a) a distal folding disk made of polyurethane or woven fabric on a wire skeleton,
   b) a proximal folding disk made of polyurethane or woven fabric on a wire skeleton,
   c) the distal folding disk is connected to the proximal folding disk by an elastic thread and a NYLON security thread,
   d) the elastic thread has a length of 1-2 mm at rest and 10 mm under tension and the NYLON thread has a length of 10 mm,
   e) a release wire, connected to a 1 mm suture loop which is connected to the bottom of the proximal disk.

3. A method of occluding a heart defect through a heart structure comprising the steps of:
   a) attaching a distal occluder to a string having a series of buttons,
   b) connecting a proximal occluder to the string,
   c) placing the distal occluder on a distal side of the heart structure,
   d) placing the proximal occluder on a proximal side of the heart structure, and
   e) adjusting a length of string between the disks to the approximate thickness of the heart structure by
   f) moving the proximal occluder over the series of buttons on the string until the occluders are in the occluding position, thereby
   g) holding the distal occluder in an occluding position over the defect on the distal side, and
   h) holding the proximal occluder in an occluding position over the defect on the proximal side.

4. A method of occluding a heart defect through a heart structure comprising the steps of:
   a) attaching a distal occluder to an elastic string,
   b) connecting a proximal occluder to the elastic string,
   c) placing the distal occluder on a distal side of the heart structure, d) placing the proximal occluder on a proximal side of the heart structure, and e) adjusting a length of string between the disks to the approximate thickness of the heart structure by f) stretching the elastic string to position the proximal occluder, thereby g) holding the distal occluder in an occluding position over the defect on the distal side, and h) holding the proximal occluder in an occluding position over the defect on the proximal side.

* * * * *